US011523743B2

(12) United States Patent
Thakur et al.

(10) Patent No.: US 11,523,743 B2
(45) Date of Patent: Dec. 13, 2022

(54) AMBULATORY MONITORING OF PHYSIOLOGIC RESPONSE TO VALSALVA MANEUVER

(71) Applicant: Cardiac Pacemakers, Inc., St. Paul, MN (US)

(72) Inventors: Pramodsingh Hirasingh Thakur, Woodbury, MN (US); David J. Ternes, Roseville, MN (US); Ashley Moriah Jensen, Roseville, MN (US); Qi An, Blaine, MN (US); Amy Jean Brisben, Saint Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 639 days.

(21) Appl. No.: 16/515,740

(22) Filed: Jul. 18, 2019

(65) Prior Publication Data
US 2020/0037887 A1 Feb. 6, 2020

Related U.S. Application Data

(60) Provisional application No. 62/714,413, filed on Aug. 3, 2018.

(51) Int. Cl.
*A61B 5/021* (2006.01)
*A61B 5/0205* (2006.01)
(Continued)

(52) U.S. Cl.
CPC ............ *A61B 5/021* (2013.01); *A61B 5/0205* (2013.01); *A61B 5/113* (2013.01); *A61B 5/1116* (2013.01);
(Continued)

(58) Field of Classification Search
CPC ..... A61B 5/021; A61B 5/0205; A61B 5/1116; A61B 5/113; A61B 5/686; A61B 5/7275;
(Continued)

(56) References Cited

U.S. PATENT DOCUMENTS 6,120,442 A * 9/2000 Hickey ................ A61B 5/0215
600/587
7,387,610 B2 6/2008 Stahmann et al.
(Continued)

OTHER PUBLICATIONS

Thakur, Pramodsingh Hirasingh, et al., "Ambulatory Monitoring of Physiologic Response to Valsalva Maneuver", U.S. Appl. No. 16/515,740, filed Jul. 18, 2019.
(Continued)

*Primary Examiner* — Aaron F Roane
(74) *Attorney, Agent, or Firm* — Schwegman Lundberg & Woessner, P.A.

(57) ABSTRACT

Systems and methods for monitoring physiologic response to Valsalva maneuver (VM) are disclosed. An exemplary patient monitor may detect a natural incidence of a VM session occurred in an ambulatory setting using a heart sound (HS) signal sensed from the patient. The patient monitor may include a physiologic response analyzer to sense patient physiologic response during the detected VM session, and generate a cardiovascular or autonomic function indicator based on the sensed physiologic response to the VM. Using the physiologic response to the VM, the system may detect a target physiologic event using the sensed physiologic response to the VM.

20 Claims, 6 Drawing Sheets

(51) Int. Cl.
    *A61B 5/00*     (2006.01)
    *A61B 5/113*     (2006.01)
    *A61N 1/39*     (2006.01)
    *A61B 5/11*     (2006.01)
    *A61N 1/365*     (2006.01)
    *A61B 5/0285*     (2006.01)
    *A61B 5/02*     (2006.01)
    *A61B 5/08*     (2006.01)
    *A61B 5/024*     (2006.01)
    *A61N 1/37*     (2006.01)
    *A61B 5/053*     (2021.01)
    *A61N 1/362*     (2006.01)
    *A61B 5/316*     (2021.01)
    *A61B 5/349*     (2021.01)

(52) U.S. Cl.
CPC ............ *A61B 5/686* (2013.01); *A61B 5/7275* (2013.01); *A61N 1/3904* (2017.08); *A61B 5/0031* (2013.01); *A61B 5/024* (2013.01); *A61B 5/02007* (2013.01); *A61B 5/0285* (2013.01); *A61B 5/053* (2013.01); *A61B 5/0816* (2013.01); *A61B 5/316* (2021.01); *A61B 5/349* (2021.01); *A61B 5/4035* (2013.01); *A61N 1/3627* (2013.01); *A61N 1/36514* (2013.01); *A61N 1/36585* (2013.01); *A61N 1/3702* (2013.01)

(58) Field of Classification Search
CPC ....... A61B 5/349; A61B 5/316; A61B 5/0031; A61B 5/02007; A61B 5/024; A61B 5/0285; A61B 5/053; A61B 5/0816; A61B 5/4035; A61N 1/3904; A61N 1/3627; A61N 1/36514; A61N 1/36585; A61N 1/3702

USPC ....................................................... 600/509
See application file for complete search history.

(56) References Cited

U.S. PATENT DOCUMENTS

| | | | |
|---|---|---|---|
| 7,488,290 B1* | 2/2009 | Stahmann | A61B 5/021 600/500 |
| 9,220,444 B2 | 12/2015 | Russell | |
| 10,159,439 B2 | 12/2018 | Hyde et al. | |
| 10,231,667 B2 | 3/2019 | Mathew et al. | |
| 10,368,794 B2 | 8/2019 | Ionescu et al. | |
| 10,405,819 B2 | 9/2019 | Arima | |
| 2006/0155204 A1* | 7/2006 | Wariar | A61B 5/021 600/528 |
| 2006/0287604 A1* | 12/2006 | Hickey | A61B 7/026 600/528 |
| 2018/0325431 A1 | 11/2018 | Guarin et al. | |
| 2019/0104989 A1 | 4/2019 | Breaux et al. | |
| 2019/0274655 A1 | 9/2019 | Thakur et al. | |
| 2021/0204874 A1 | 7/2021 | Thakur et al. | |

OTHER PUBLICATIONS

Burroughs, Robert W., et al., "Significance of Abnormal Phase II Response to Valsalva Maneuver in Cardiac Patients", Circulation. 1956;14:72-76.

Nwazue, Victor C., et al., "Confounders of Vasovagal Syncope: Orthostatic Hypotension", Cardiol Clin. Feb. 2013; 31(1): 89-100. doi:10.1016/j.ccl.2012.09.003.

Singh, Mohita, "Valsalva ratio: Assessment of autonomic modulation in patients of cervical spondylosis", IAIM, 2016; 3(6): 107-112.

* cited by examiner

AMBULATORY MONITORING OF PHYSIOLOGIC RESPONSE TO VALSALVA MANEUVER

CLAIM OF PRIORITY

This application claims the benefit of priority under 35 U.S.C. § 119(e) of U.S. Provisional Patent Application Ser. No. 62/714,413, filed on Aug. 3, 2018, which is herein incorporated by reference in its entirety.

TECHNICAL FIELD

This document relates generally to medical devices, and more particularly, to systems, devices and methods for ambulatory detection of Valsalva maneuver and monitoring physiologic response to Valsalva maneuver.

BACKGROUND

Valsalva maneuver (VM) is a technique typically performed when one attempts to exhale forcefully against a closed airway, such as by closing one's mouth or pinching one's nose shut. The VM can occur unintentionally or intentionally. Natural incidence of VM may occur when sneezing, coughing, passing stool during constipation, vomiting, lifting heavy objects (e.g., weightlifting or other fitness regimes), or getting up from the bed. VM technique has been used to equalize the ear pressure during activities like scuba diving, flight landing, parachuting etc.

The VM can increase pressures inside the nasal sinuses and the chest cavity within a short period of time. Sustained elevated chest pressure may stimulate the vagus nerve and increase vagal tone. Physiologic response to the VM typically consists of four phases. In Phase I, blowing against a closed airway increases the pressure inside the chest cavity, which immediately pushes blood from the pulmonary circulation into the left atrium of the heart. This causes a mild rise in stroke volume during the first few seconds of the maneuver. Phase II is characterized by reduced venous return and compensation. The increased pressure in the chest cavity prevents any more blood from returning the heart from the rest of the body. As such, stroke volume suddenly falls, and cardiac output reduces. To compensate for the drop in cardiac output, the body's blood vessels constrict, and blood pressure rises. This elevated blood pressure continues for the duration of the Valsalva maneuver. In certain cases, the compensation can be quite marked with pressure returning to near or even above normal. However, the cardiac output and blood flow to the body remains low. During this time, the pulse rate increases (compensatory tachycardia). Phase III is a pressure release phase, during which the pressure on the chest is released, allowing the pulmonary vessels and the aorta to re-expand, which causes a further initial slight fall in stroke volume due to decreased left atrial return and increased aortic volume, respectively. Venous blood can once more enter the chest and the heart, and the cardiac output begins to increase. Finally, in Phase IV, the blood flow to the heart and lungs returns to normal, as does the cardiac output and blood pressure. The blood return may be enhanced by the effect of entry of blood that had been dammed back, causing a rapid increase in cardiac output. In some instances, the stroke volume may rise above normal before returning to a normal level. With return of blood pressure, the pulse rate returns towards normal.

Valsalva maneuver has been used as a diagnostic tool or a treatment aid. In an example, the VM can be used to evaluate cardiac function or autonomic nervous control of the heart. Deviation from typical response pattern of a normal healthy subject may indicate heart anomaly, or abnormal autonomic nervous control of the heart. For example, cardiovascular response to the VM may be used to evaluate cardiac filling pressure in patients with congestive heart failure (CHF). VM may also induce changes in cerebrovascular variables within a short time span, which can be used to assess cerebral autoregulatory function by provoking blood pressure changes. Other diagnostic applications include ailments related to an autonomous nervous system, nerve tissue injury in the cervical spine region, hernia, pelvic floor weakness, cerebrospinal fluid leak, intrinsic sphincteric deficiency, or abnormal connections between the mouth and maxillary sinuses (oroantral fistulas) after a tooth extraction, among others. Apart from applications in medical diagnostics, the VM has also been used as a treatment aid, such as to clear mucus and relieve pain in sinusitis, expel pus from a clogged ear in middle ear infection, interrupt palpitations such as supraventricular tachycardia, stop hiccups, etc.

Overview

The VM has been used clinically to evaluate various cardiovascular and neurological disorders, an example being detection and assessment of syncope. Syncope is generally characterized by an abrupt loss of consciousness with a concomitant loss of postural tone. Decreased cerebral perfusion is common to all causes of syncope. For example, positional change from supine to erect causes a 300- to 800-milliliter shift in blood volume from the thoracic cavity to the lower extremities. Although cerebrovascular autoregulation in healthy subjects help ensure enough cerebral blood flow independent of systemic blood pressure, older patients and those with chronic hypertension or cardiovascular diseases may be susceptible to syncope when a relatively small decrease in systemic blood pressure occurs.

Based on the underlying causes, syncope may have three major types: cardiogenic, orthostatic, and neurally mediated syncope. Cardiogenic syncope is associated with significantly higher rates of morbidity and mortality than other causes. Patients with underlying cardiac disease, such as cardiac arrhythmias or structural cardiopulmonary diseases, are at higher risk for recurrent syncope than are other syncope patients. Patients with syncope are more likely to have coronary artery or cerebrovascular disease and to take cardiac or antihypertensive medications than patients without syncope. Orthostatic syncope is associated with orthostatic hypotension (OH), characterized by a drop in blood pressure of at least 20 millimeters of mercury (mmHg) systolic or 10 mmHg diastolic within about three minutes of standing. Tachycardia and a heart rate greater than 100 beats per minute during testing indicate volume depletion. Minimal cardiac acceleration suggests baroreflex impairment may contribute to orthostatic syncope. Neurally mediated syncope, also known as vasovagal syncope (VVS), or neurocardiogenic syncope, is a disorder of the autonomic regulation of postural tone, and may be related to vasovagal, carotid sinus, or situational causes of hypotension. In healthy subjects, upon positional change, a series of complex neurohormonal events would maintain cerebral perfusion. For example, decreased venous return and subsequent decreased left ventricular filling may result in increased sympathetic tone and a hypercontractile left ventricle. However, overly sensitive left ventricular receptors may misinterpret hypercontractility as volume overload and falsely inhibit sympathetic stimulation while promoting parasympathetic drive, resulting in hypotension and syncope.

While the cardiogenic syncope constitutes only approximately 15 percent of overall syncope population, the majority of syncope are non-cardiac in nature, including about 60 percent being neurally mediated syncope, and about 15 percent being orthostatic syncope. Identifying the cause or type of syncope, such as a differential diagnosis of non-cardiac or unexplained syncope (e.g., distinguishing orthostatic syncope from VVS), may be clinically desired for improved patient management and treatment. Physiologic response to VM as discussed in this document may improve differential diagnosis of syncope. For example, patients with OH may not be able to produce sufficient increase in sympathetically mediated vasoconstriction following initial hypotension. These patients typically lack BP recovery at the late Phase II of MV and BP overshoot at the Phase IV of MV. Instead, the BP slowly drifts back up to baseline after the Valsalva-induced hypotension.

Currently, VM induction and VM response assessment are typically carried out in a clinical setting, where the patient is required to be sedentary with VM testing and analysis equipment attached to the patient. This can be less convenient for ambulatory patients who require ambulatory monitoring for syncope. Additionally, in-clinic syncope evaluation, such as orthostatic challenge or tilt-table test to identify the nature of a syncope episode occurred in the past, at least because the in-clinic tests that attempt to mimic the OH may not adequately reproduce the hemodynamic profile of the past spontaneous syncope from onset to full development. The tilt table test may have substantial false negative rate for detecting syncope onset in a clinical test. At least because many syncopal events occur abruptly and unexpectedly in an ambulatory setting, ambulatory syncope monitoring or and differential diagnosis of syncope types, based on naturally occurring VM sessions, may be clinically advantageous in some patients. For these reasons, the present inventors have recognized that there is a need for improved systems, devices, and methods for ambulatory VM monitoring and clinical diagnosis based on patient ambulatory VM responses.

This document discusses, among other things, systems, devices, and methods for monitoring patient physiologic response to the VM. An exemplary patient monitor includes a VM detector circuit to detect a VM session, such as a naturally occurring VM incidence, using a heart sound (HS) signal sensed from the patient. The patient monitor may include a physiologic response analyzer circuit to sense a physiologic response to the detected VM session, and generate a cardiovascular or autonomic function indicator based on the physiologic response to the VM. The system can generate medical diagnostics such as a syncope of a particular type, a worsening heart failure (WHF) event, or a constipation episode.

Example 1 is a system for monitoring a physiologic response to a Valsalva maneuver (VM) in a patient. The system comprises a VM detector circuit configured to detect a VM session using a heart sound (HS) signal sensed from the patient, a physiologic response analyzer circuit configured to sense a physiologic signal during the detected VM session, and a physiologic event detector configured to detect a target physiologic event using the sensed physiologic signal during the detected VM session.

In Example 2, the subject matter of Example 1 optionally includes the VM detector circuit configured to recognize one or more VM phases using a HS metric based on one or more of first (S1), second (S2), third (S3), or fourth (S4) heard sound component from the sensed HS signal, the VM phase including sequentially arranged first, second, third, or fourth VM phases.

In Example 3, the subject matter of Example 2 optionally includes the VM detector circuit configured to detect one or more of: the first VM phase using an increase in S1 intensity and a decrease in S2 intensity: the second VM phase using a decrease in S1 intensity and an increase in S2 intensity; or the fourth VM phase using an increase in S1 intensity and an increase in S2 intensity.

In Example 4, the subject matter of any one or more of Examples 2-3 optionally includes the VM detector circuit configured to detect one or more of: the first VM phase using an increase in S3 intensity or an increase in S4 intensity; or the third VM phase using a decrease in S3 intensity or a decrease in S4 intensity.

In Example 5, the subject matter of any one or more of Examples 2-4 optionally includes the VM detector circuit configured to detect the VM session further using one or more of: a physical activity level below a specific threshold; an upright posture; or a respiratory pause.

In Example 6, the subject matter of any one or more of Examples 2-5 optionally includes the physiologic response analyzer circuit configured to generate a cardiovascular or autonomic function indicator using the sensed physiologic signal during the detected VM session, the sensed physiologic signal includes one or more of a HS signal and a heart rate signal.

In Example 7, the subject matter of Example 6 optionally includes the physiologic response analyzer circuit configured to generate the cardiovascular or autonomic function indicator using a comparison of the sensed physiologic signal during the detected VM session to a Valsalva response template at one or more of the VM phases.

In Example 8, the subject matter of any one or more of Examples 2-7 optionally includes the physiologic response analyzer circuit configured to detect S3 intensity and S4 intensity from a HS signal sensed during the detected VM session, and to generate a diastolic dysfunction indictor using a ratio of the S3 intensity to the S4 intensity.

In Example 9, the subject matter of Example 8 optionally includes the physiologic event detector configured to detect a worsening heart failure (WHF) event using the generated diastolic dysfunction indictor.

In Example 10, the subject matter of any one or more of Examples 6-7 optionally includes the physiologic event detector configured to detect a syncope using the generated cardiovascular or autonomic function indicator.

In Example 11, the subject matter of Example 10 optionally includes the cardiovascular or autonomic function indicator that may include a Valsalva ratio using heart rates measured during the detected VM session, and the physiologic event detector may be configured to detect a vasovagal syncope using the generated Valsalva ratio.

In Example 12, the subject matter of Example 10 optionally includes the cardiovascular or autonomic function indicator that may include a S2 intensity trend during the detected VM session, and the physiologic event detector may be configured to detect an orthostatic syncope using the generated S2 intensity trend.

In Example 13, the subject matter of any one or more of Examples 2-7 optionally includes the physiologic event detector configured to detect the target physiologic event including a constipation episode.

In Example 14, the subject matter of any one or more of Examples 1-13 optionally includes a therapy circuit configured to initiate or adjust a therapy to the patient in response to the detected target physiologic event.

In Example 15, the subject matter of any one or more of Examples 1-14 optionally includes an ambulatory medical device (AMD) including the VM detector circuit and the physiologic response analyzer circuit, the AMD configured to monitor a patient physiologic response to the detected VM session.

Example 16 is a method for monitoring a physiologic response to a Valsalva maneuver (VM) in a patient. The method comprises steps of: detecting a VM session using a heart sound (HS) signal sensed from the patient; sensing a physiologic signal during the detected VM session; and detecting a target physiologic event using the sensed physiologic signal during the detected VM session.

In Example 17, the subject matter of Example 16 optionally includes detecting the VM session that may include recognizing one or more VM phases using a HS metric based on one or more of first (S1), second (S2), third (S3), or fourth (S4) heard sound component from the sensed HS signal, the VM phase including sequentially arranged first, second, third, or fourth phases.

In Example 18, the subject matter of Example 17 optionally includes recognizing the one or more VM phases that may include detecting one or more of: the first VM phase using an increase in S1 intensity and a decrease in S2 intensity, or an increase in S3 intensity or an increase in S4 intensity; the second VM phase using a decrease in S1 intensity and an increase in S2 intensity; the third VM phase using a decrease in S3 intensity or a decrease in S4 intensity; or the fourth VM phase using an increase in S1 intensity and an increase in S2 intensity.

In Example 19, the subject matter of any one or more of Examples 16-18 optionally includes detecting a VM session that may include detecting one or more of: a physical activity level below a specific threshold; an upright posture; or a respiratory pause.

In Example 20, the subject matter of any one or more of Examples 16-19 optionally includes generating a cardiovascular or autonomic function indicator using a comparison of the sensed physiologic signal during the detected VM session to a Valsalva response template, the sensed physiologic signal includes one or more of a HS signal and a heart rate signal.

In Example 21, the subject matter of Example 20 optionally includes detecting the target physiologic event that may include detecting a syncope using the generated cardiovascular or autonomic function indicator.

In Example 22, the subject matter of any one or more of Examples 16-21 optionally includes detecting the target physiologic event that may include: detecting S3 intensity and S4 intensity from a HS signal sensed during the detected VM session; generating a diastolic dysfunction indictor using a ratio of the S3 intensity to the S4 intensity; and detecting a worsening heart failure (WHF) event using the generated diastolic dysfunction indictor.

In Example 23, the subject matter of any one or more of Examples 16-22 optionally includes initiating or adjusting a therapy to the patient in response to the detected target physiologic event.

The systems, devices, and methods discussed in this document may improve the technology of ambulatory monitoring of physiologic response to VM, and detection of patient cardiovascular or neurological condition based on the ambulatory VM response. Discussed herein includes detecting and assessing a physiologic, naturally occurring VM session using heart sounds (HS). The present inventors have recognized that various HS metrics are indicative of or correlated with hemodynamic profiles at various VM phases (e.g., one or more of Phases I-IV). As such, using HS is advantageous in recognizing a deviation from a normal physiologic response at one or more VM phases. Compared to conventional in-clinic approach of inducing VM and analyzing patient cardiovascular response to the VM, the systems and methods discussed in this document may be more suitable for patients with such medical conditions that require ambulatory monitoring, such as WHF events and syncope episodes. The HS-based VM response monitor may improve the performance of a physiologic event detector, with a higher sensitivity and specificity for detecting events such as WHF or syncope episodes. This may help ensure timely medical attention to patients and medical intervention as needed, and reduce unnecessary medical interventions (e.g., drugs, procedures, or device therapies) to those patients identified to be free of the medical events or have a low risk of developing such events in the future. Additionally, the HS-based VM monitoring and differential diagnosis of syncope may help ensure individualized syncope therapy. As such, the devices and methods discussed herein would not only better align the medical resources to serve the need of more patients, but may also achieve overall system cost savings for chronically monitoring syncope patients.

The systems, devices, and methods discussed in this document may also improve functionality of a medical device or a patient management system. Conventional cardiovascular monitoring during the VM may put a high demand for battery power, storage space, computing and process power, and communication bandwidth. In contrast, HS sensors have been used for ambulatory cardiac monitoring. HS sensors can be non-invasively attached to the patient. The HS-based VM response detection discussed herein requires little extra hardware beyond what an ambulatory cardiac monitor may generally provide. Therefore, the HS-based VM monitoring system discussed herein provides a power- and resource-conservative solution to ambulatory VM response monitoring.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for monitoring physiologic response to Valsalva maneuver (VM). An exemplary patient monitor may detect a natural incidence of VM session using a heart sound (HS) signal sensed from the patient. The patient monitor includes a physiologic response analyzer circuit that can sense patient physiologic response during the detected VM session, and generate a cardiovascular or autonomic function indicator based on the sensed physiologic response to the VM. Based on the physiologic response, the system may detect a target physiologic event.

Figure 1:
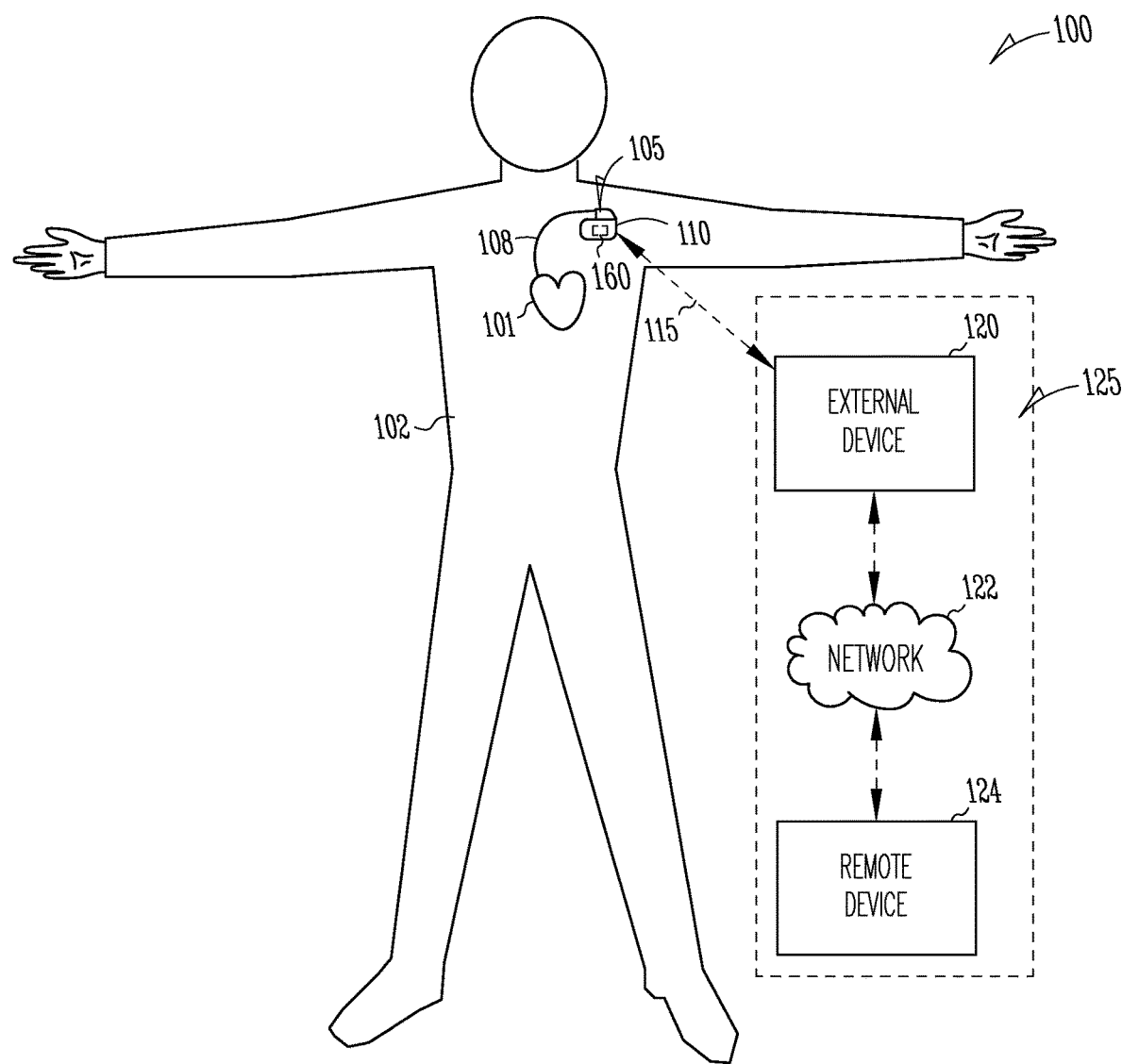
FIG. 1 illustrates generally an example of a patient monitor system and portions of an environment in which the system may operate.

FIG. 1 illustrates generally an example of a patient monitor system 100 and portions of an environment in which the system 100 may operate. The patient monitor system 100 may chronically monitor a patient 102 to detect and evaluate a syncopal event. Portions of the system 100 may be ambulatory. Portions of the system 100 may be disposed in the patient's home or office, a hospital, clinic, or physician's office. The patient monitor system 100 may include an ambulatory system 105 associated with the patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart wearables, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic response to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may include a hermetically sealed can that houses one or more of a sensing circuit, a control circuit, a communication circuit, and a battery, among other components. The sensing circuit may sense a physiologic signal, such as by using a physiologic sensor or the electrodes associated with the lead system 108. The physiologic signals may contain information about patient physiologic response to a precipitating event associated with onset of a future syncopal event. The physiologic signal may represent changes in patient hemodynamic status. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a Valsalva maneuver (VM) response analyzer circuit 160 that can detect a VM session such as a naturally occurring VM incidence, and evaluate patient physiologic response to the VM. The VM session may be detected using a heart sounds (HS) signal sensed from the patient. HS metrics, indicative of or correlated to hemodynamic profiles during the VM, may be generated from the HS signal. The VM response analyzer circuit 160 may use the HS metrics to determine a deviation from a normal VM response at one or more VM phases. The VM response analyzer circuit 160 may sense patient physiologic response to the detected VM session, and generate a cardiovascular or autonomic function indicator, detect a target physiologic event such as WHF, heart murmur, syncope, or constipation. Examples of detecting the VM, and detecting a physiologic event using the physiologic response to the VM, are discussed below, such as with reference to FIGS. 2-4.

The AMD 110 may include a therapy circuit configured to generate and deliver a therapy to the patient, such as in response to the detected physiologic event. Examples of the therapy may include electrical, magnetic, or other forms of therapy. In some examples, the patient monitor system 100 may include a drug delivery system, such as a drug infusion pump, to deliver medication, such as diuretics or vasodilators for treating or alleviating symptoms of HF. The AMD 110 may trend the physiologic response to the VM over time, and use said trend to assess progression of a medical condition (e.g., WHF), predict a risk of a future event (e.g., HF decompensation, or syncope), assess a therapeutic effect of a therapy (e.g., a device therapy such as provided by the AMD 110, or a drug therapy such as provided by the drug delivery system 116), or modify a therapy if needed.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect VM and a target physiologic event, or optionally delivering or adjusting a therapy to the patient 102. The external system 125 may communicate with the AMD 110 via the communication link 115. The device data received by the external system 125 may include real-time or stored physiologic data from the patient 102, diagnostic data such as cardiovascular or autonomic function indicator or detected physiologic event, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device. The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

The remote device 124 may include a centralized server acting as a central hub for collected patient data storage and analysis. The patient data may include data collected by the AMD 110, and other data acquisition sensors or devices associated with the patient 102. The server may be configured as a uni-, multi-, or distributed computing and processing system. In an example, the remote device 124 may include a data processor configured to perform further data analysis, such as detection of a target physiologic event, using the signals received by the AMD 110. Computationally intensive algorithms, such as machine-learning algorithms, may be implemented in the remote device 124 to process the data retrospectively to confirm, reject, or modify the target physiologic event detection provided by the AMD 110. The remote device 124 may generate an alert notification. The alert notifications may include a Web page update, phone or pager call, E-mail, SMS, text or "Instant" message, as well as a message to the patient and a simultaneous direct notification to emergency services and to the clinician. Other alert notifications are possible.

One or more of the external device 120 or the remote device 124 may output the cardiovascular or autonomic function indicator or the detected target physiologic event to a system user such as the patient or a clinician. The clinician may review, perform further analysis, or adjudicate the device detection. The detected cardiovascular or autonomic function indicator during the VM, optionally along with the HS metrics and other physiologic data, may be output to a process including an instance of a computer program executable in a microprocessor. In an example, the process may include an automated generation of recommendations for initiating or adjusting a therapy, or a recommendation for further diagnostic test or treatment. In an example, the external device 120 or the remote device 124 may include a respective display unit for displaying the physiologic and hemodynamic signals, or alerts, alarms, emergency calls, or other forms of warnings about the detection and classification of a syncopal event.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
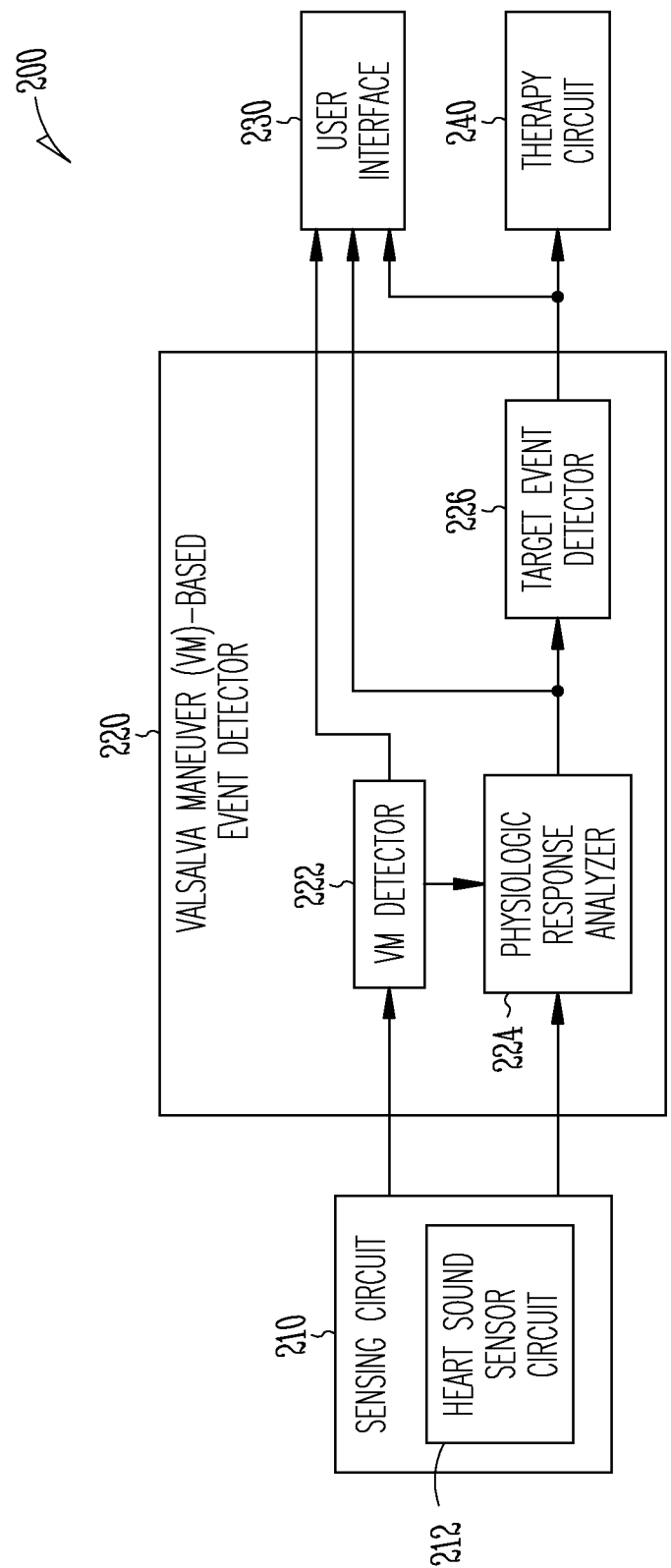
FIG. 2 illustrates generally an example of a Valsalva maneuver (VM) detector and analyzer system configured to detect a VM session and evaluate patient physiologic response to the VM.

FIG. 2 illustrates generally an example of a Valsalva maneuver (VM) detector and analyzer system 200 configured to detect a VM session and evaluate patient physiologic response to the VM. At least a portion of the VM detector and analyzer system 200 may be implemented in the AMD 110, the external system 125 such as one or more of the external device 120 or the remote device 124, or distributed between the AMD 110 and the external system 125.

As illustrated in FIG. 2, the VM detector and analyzer system 200 may include one or more of a sensing circuit 210, a VM-based event detector 220, a user interface 230, and an optional therapy circuit 240. The sensing circuit 210 may sense a physiologic signal from the patient. In an example, the sensing circuit 210 may include a sense amplifier circuit to sense the physiologic signal from a patient via a physiologic sensor, such as an implantable, wearable, or otherwise ambulatory sensor or electrodes associated with the patient. The sensor may be incorporated into, or otherwise associated with an ambulatory device such as the AMD 110. In some examples, the physiologic signals sensed from a patient may be stored in a storage device, such as an electronic medical record (EMR) system. The sensing circuit 210 may receive the physiologic signal from the storage device, such as in response to a user command or a triggering event. Examples of the physiologic signals for detecting the precipitating event may include surface electrocardiography (ECG) sensed from electrodes placed on the body surface, subcutaneous ECG sensed from electrodes placed under the skin, intracardiac electrogram (EGM) sensed from the one or more electrodes on the lead system 108, heart rate signal, physical activity signal, or posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensing circuit 210 may include one or more sub-circuits to digitize, filter, or perform other signal conditioning operations on the received physiologic signal.

In an example, the sensing circuit 210 may include a heart sound (HS) sensor circuit 212 configured to generate one or more HS metrics using HS information of the patient. The sensing circuit 210 may be communicatively coupled to a heart sound sensor to sense a HS signal. The HS sensor may take the form of an accelerometer, an acoustic sensor, a microphone, a piezo-based sensor, or other vibrational or acoustic sensors. The accelerometer can be a two-axis or a three-axis accelerometer. Examples of the accelerometer may include flexible piezoelectric crystal (e.g., quartz) accelerometer or capacitive accelerometer, fabricated using micro electro-mechanical systems (MEMS) technology. The HS sensor may be included in the AMD 110, or disposed on a lead such as a part of the lead system 108. In an example, the accelerometer may sense an epicardial or endocardial acceleration (EA) signal from a portion of a heart, such as on an endocardial or epicardial surface of one of a left ventricle, a right ventricle, a left atrium, or a right atrium. The EA signal may contain components corresponding to various HS components.

The HS sensor circuit 212 may filter the sensed HS signal through a filter. In an example, the filter may be band-pass filter having a pass-band frequency of approximately between 5 and 90 Hz, or approximately between 9 and 90 Hz. In an example, the filter may include a double or higher-order differentiator configured to calculate a double or higher-order differentiation of the heart sound signal. The HS analyzer circuit may compute an ensemble average of the HS signal over multiple cardiac cycles, or over a specified time period that is expected to encompass multiple VM sessions. One or more HS components may be detected from the HS signal, including a first (S1) heart sound, a second (S2) heart sound, a third (S3) heart sound, or a fourth (S4) heart sound using respective time windows. S1 is associated with the vibrational sound made by the heart during tensing of the mitral valve. S2 is produced by the closure of the aortic and pulmonary valves, and marks the beginning of diastole. S3 is an early diastolic sound corresponding to passive ventricular filling during diastole, when the blood rushes into the ventricles. S4 is a late diastolic sound corresponding to active ventricular filling when the atria contract and push the blood into the ventricles.

The HS sensor circuit 212 may generate one or more HS metrics using the detected HS components. Examples of the HS metrics may include an intensity (e.g., amplitude or signal energy under the curve) of a HS component, or one or more HS-based cardiac timing intervals, such as a pre-ejection period (PEP) such as measured between the onset of the QRS to the S1 heart sound, a systolic timing interval (STI) such as measured between the onset of the QRS complex on the ECG to the S2 heart sound, a left-ventricular ejection time (LVET) such as measured as an interval between S1 and S2 heart sounds, or a diastolic timing interval (DTI) such as measured between the S2 heart sound and the onset of the subsequent QRS complex on the ECG, among others. These HS-based cardiac timing intervals may be correlated with cardiac contractility or cardiac diastolic function of the heart. The HS metrics may further include PEP/LVET ratio, STI/DTI ratio, STI/cycle length (CL) ratio, or DTI/CL ratio, or other composite metrics.

The VM-based event detector 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The VM-based event detector 220 may include circuit sets comprising one or more other circuits or sub-circuits, such as a VM detector 222, a physiologic response analyzer 224, and a target event detector 226. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The VM detector 222 may detect a VM session, such as a physiologic, naturally occurring VM incidence in an ambulatory patient, using one or more sensed physiologic signals provided by the sensing circuit 210. In a non-limiting example, the VM detector 222 may detect a VM session using one or more HS metrics produced by the heart sound sensor circuit 212. As discussed above, a typical VM process consists of up to four temporal phases each having distinct hemodynamic profiles, such as distinct blood pressure or heart rate patterns at the VM phases. The hemodynamic profiles reflect sympathetic and parasympathetic activities during the VM. The present inventors have recognized that various HS metrics may be indicative of or correlated to the hemodynamic profiles at various VM phases. The VM detector 222 may use the HS metrics to detect an onset, one or more temporal phases, or termination of the VM session. For example, S1 intensity is correlated to cardiac contractility, and S2 intensity is correlated to blood pressure. The VM detector 222 may trend S1 intensity or S2 intensity over a period of time of approximately 10-30 seconds, and detect a VM session (or a VM phase) using the trended S1 intensity, the trended S2 intensity, or a combined S1 trend and S2 trend.

By way of example and not limitation, the VM detector 222 may detect Phase I of VM using an increase in S1 intensity accompanied by a decrease in S2 intensity. The increase in S1 at Phase I may be resulted from an increased venous return, which leads to an increase in cardiac contractility; and the decrease in S2 represents an initial progressive reduction in blood pressure. The VM detector 222 may detect Phase II of the VM using a decrease in S1 intensity and an increase in S2 intensity. The decrease in S1 intensity corresponds to reduced stroke volume and cardiac output, which leads to reduced cardiac contraction. The increase in S2 intensity at Phase II corresponds to the rise in blood pressure due to vasoconstriction to compensate for the drop in cardiac output. The VM detector 222 may detect Phase IV of the VM using an increase in S1 intensity accompanied by an increase in S2 intensity. This corresponds to the recovery of cardiac output and blood pressure at the closing phase of VM.

In addition to or in lieu of S1 and S2, in some examples, the VM detector 222 may detect one or more temporal phases of a VM session using measurements of S3 intensity or S4 intensity. S3 or S4 intensity indicates diastolic function of a heart, and is correlated to left-ventricular filling pressure or the left atrial pressure (LAP) at the end of diastole, particularly in a heart failure patient. In an example, the VM detector 222 may detect Phase I of VM using an increase in S3 intensity or an increase in S4 intensity, which correspond to immediate accumulation of blood in the left atrium of the heart and thus a rise in LAP. Phase III of VM is characterized by thoracic pressure release and widening of intrathoracic arteries and aorta, which may help reduce LAP and end-diastolic left ventricular pressure. The VM detector 222 may detect Phase III using a decrease in S3 intensity or a decrease in S4 intensity. Apart from the intensities S1, S2, S3, or S4 as discussed above, other HS metrics, such as PEP, STI, LVET, or other cardiac timing parameters that are correlated with cardiac contractility or left-ventricular diastolic function, may additionally or alternatively be used to detect a VM session or a particular temporal phase of VM.

The VM detector 222 may detect a VM session, or a portion thereof (e.g., one or more VM phases), using physiologic information in addition to or in lieu of the HS information as discussed above. The physiologic information may be extracted from the received physiologic signal. In various examples, the VM detector 222 may detect a VM session using information such as abdominal muscle strain (such as sensed using a strain gauge), respiration information (such as sensed using thoracic impedance sensor, a flowmeter, or a tracheal noise sensor), heart rate and blood pressure, or information about neural activities. In some examples, additional sensors may be used to improve signal quality of the HS data acquired during the VM session, or to confirm the VM session detected using the HS metrics. Examples of detecting VM using additional sensors in conjunction with HS information are discussed below, such as with reference to FIG. 3.

The physiologic response analyzer 224 may be coupled to the sensing circuit 210 and the VM detector 222, and configured to detect a patient physiologic response to the VM session as detected by the VM detector 222. In an example, the physiologic response analyzer 224 may use HS signals to determine the physiologic response to the VM. The HS signals may be the same signals used by the VM detector 222 for detecting the VM session or various VM phases, or different HS signals acquired by the same HS sensors that provide the HS signal to the VM detector 222. In an example, the physiologic response analyzer 224 may generate a cardiovascular or autonomic function indicator using a comparison of the sensed physiologic signal to a reference VM response (hereinafter referred to as VM response template). The VM response template may be generated using physiologic data (e.g., HS data) acquired from the patient during historical VM sessions, thus representing the patient's baseline VM response. Alternatively, the VM response template may be generated using data from population during the VM sessions, thus presenting a "normal" VM response. In an example, the physiologic response analyzer 224 may determine a degree of deviation of the patient physiologic data trend (e.g., a S1 intensity trend or a S2 intensity trend) from the VM response template. The deviation may be computed using an accumulated difference between the physiologic data trend and the VM response template over the entirety, or a portion (e.g., one or more temporal phases), of the VM session. The physiologic response analyzer 224 may generate the cardiovascular or autonomic function indicator indicating a blunted cardiovascular or autonomic function if the determined degree of deviation exceeds a threshold.

In some examples, the sensing circuit 210 may sense one or more physiologic signals in addition to the HS. The physiologic response analyzer 224 may determine the physiologic response to the VM using the sensed physiologic signals in lieu of, or in addition to, the HS signal. In an example, the physiologic response analyzer 224 may detect a heart rate (HR) during the detected VM. If the HR falls below a threshold, or if a decreasing trend of HR is detected, an autonomic failure is indicated. Other physiologic signals include cardiac pressure, blood pressure, cardiac or thoracic impedance, among others.

The target event detector 226 can detect a target physiologic event using the detected patient physiologic responses such as provided by the physiologic response analyzer 224. As discussed above, physiologic responses to the VM may indicate cardiovascular and autonomous functions. The cardiovascular or autonomic function indicator, or the deviation from a patient baseline VM response template or a population-based "normal" VM response template, may be used to form diagnostics of one or more medical conditions, as to be discussed in the following with reference to FIGS. 4A-4C.

The user interface 230 may include an input unit and an output unit. In an example, at least a portion of the user interface 230 may be implemented in the external system 125. The input unit may receive user input for programming the sensing circuit 210 and the VM-based event detector 220, such as parameters for detecting HS components and generating HS metrics, threshold values for determining the cardiovascular or autonomic function indicator using the deviation of physiologic response to the VM from the reference VM response template, and parameters for detecting the target physiologic event. The input unit may include a keyboard, on-screen keyboard, mouse, trackball, touchpad, touch-screen, or other pointing or navigating devices. The output unit may include a display for displaying the patient physiologic data (e.g., the HS signal and the HS metrics), the comparison between the physiologic response to the VM and the reference VM response template, the detected target events, and any intermediate measurements or computations, among others. The output unit may also present to a user, such as via a display unit, recommended therapy, such as a change of parameters in the therapy provided by an implanted device, the prescription to get a device implanted, the initiation or change in a drug therapy, or other treatment options of a patient. The output unit may include a printer for printing hard copies of signals and information of VM response and detected physiologic event. The signals and information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected medical events.

In some examples, the output unit may prompt a user for initiating or repeating a VM session. This is referred to as a commanded VM session. The sensing circuit 210 and the VM-based event detector 220 may monitor patient physiologic response to the commanded VM session, and to detect a target event. The commanded VM session may be prompted to the user periodically, or triggered by a medical event.

The optional therapy circuit 240 may be configured to deliver a therapy to the patient, such as in response to the detected physiologic event, or when the detected cardiovascular or autonomic function indicator satisfies a specific condition (e.g., indicating blunted vasovagal response or autonomic function). The therapy may be preventive or therapeutic in nature such as to modify, restore, or improve patient neural, cardiac, or respiratory functions. Examples of the therapy may include electrostimulation therapy delivered to the heart, a nerve tissue, other target tissues, a cardioversion therapy, a defibrillation therapy, or drug therapy including delivering drug to the patient. In some examples, the therapy circuit 240 may modify an existing therapy, such as adjust a stimulation parameter or drug dosage.

Figure 3:
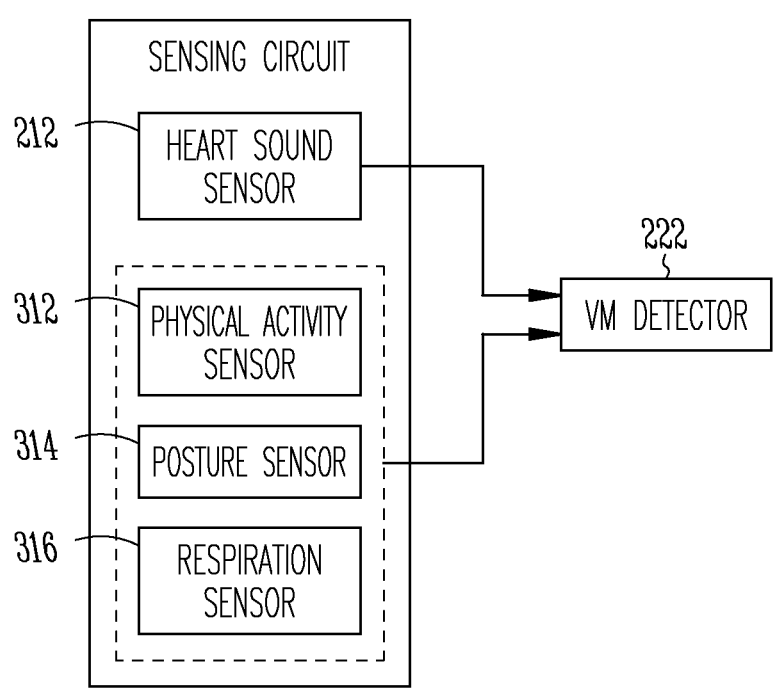
FIG. 3 illustrated generally an example of a portion of a VM detection system that detects a VM session using heart sounds and information about patient functional states.

FIG. 3 illustrated generally an example of a portion of a VM detection system that detects a VM session using heart sounds and information about patient functional states. By way of example, the patient functional states may include one or more of physical activity detected by a physical activity sensor 312, a posture detected by a posture sensor 314, or respiration detected by a respiration sensor 316. The physical activity sensor 312 may include an accelerometer configured to sense a physical activity signal. The accelerometer may be single-axis or multi-axis accelerometer. The posture sensor 314 may include a tilt switch or a single- or multi-axis accelerometer associated with the patient. For example, the posture sensor may be disposed external to the body or implanted inside the body. Posture may be represented by, for example, a tilt angle. In some examples, posture or physical activity information may be derived from thoracic impedance information. The respiration sensor may include a flowmeter that directly senses airflow in the respiratory system or volume change in the lung, a strain sensor configured to sense changes in chest muscle tension corresponding to respiration cycles, an accelerometer to measure acceleration associated with displacement or movement of chest walls corresponding to respiration, or an impedance sensor to sense thoracic impedance that is modulated by respiration.

One or more of the physical activity sensor 312, the posture sensor 314, or the respiration sensor 316 may be associated with a patient in various manners, such as implantable sensors configured for subcutaneous implantation at various body locations, or wearable sensors configured to be worn on the head, wrist, hand, foot, ankle, waist, or other parts of the body. One or more of these sensors may be used as a confirmation of patient initiating a VM session, or to improve quality of the HS data acquired during the VM session. For example, a low activity level, as detected by the physical activity sensor 312, may rule out strenuous breathing during moderate to high physical activity, as VM typically occurs when patient remains at low activity. Similarly, an upright posture is to rule out VM confounders, such as sleep apnea that may involve strenuous breathing or breathing pause during sleep. In an example, the heart sound sensor 212 is configured to acquire HS data when the physical activity sensor 312 detects a low activity level (e.g., below a threshold), the posture sensor 314 detects an upright posture, or the respiration sensor 316 detects forced breathing. Additionally or alternatively, the VM detector 222 may select portions of the HS signal acquired by the HS sensor 212 only when the low activity level, upright posture, and forced breathing are detected by the respective sensors. By using information of physical activity, posture, and detected respiration, fewer false positive detections of VM sessions may result.

Figure 4A:
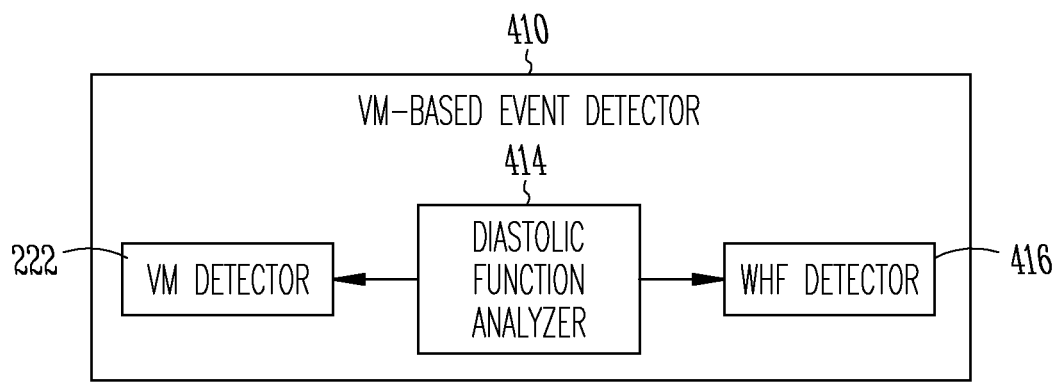
FIGS. 4A-C illustrate generally examples of VM-based physiologic event detectors configured to detect various physiologic events using physiologic response to the VM.
Figure 4B:
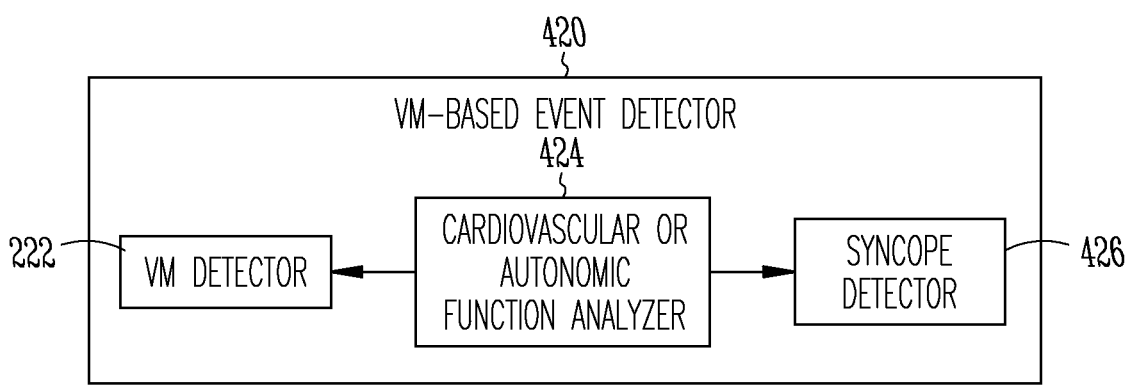
Figure 4C:
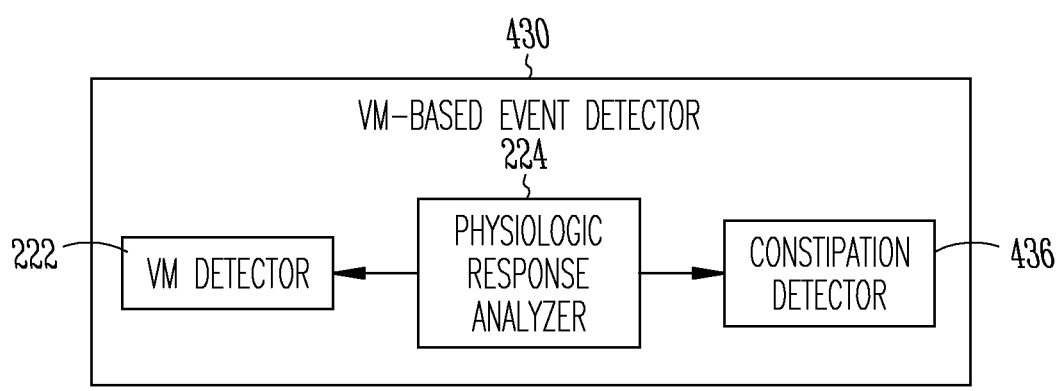

FIGS. 4A-C illustrate generally examples of VM-based physiologic event detectors 410, 420, and 430 configured to detect various physiologic events using physiologic response to the VM. The detectors 410, 420, and 430 are embodiments of the VM-based event detector 220 as illustrated in FIG. 2. FIG. 4A illustrates a VM-based event detector 410 configured to detect a target event of worsening heart failure (WHF) using the physiologic responses to the VM. The VM-based event detector 410 includes a diastolic function analyzer 414, which is an embodiment of the physiologic response analyzer 224, and configured to generate a cardiac diastolic function indicator during the detected VM. Cardiovascular response to the VM has been found to be significantly correlated with ventricular filling pressures in HF patients. An abnormal response to the VM in cardiac patients may be closely associated with clinical signs and symptoms of congestive HF. In an example, the diastolic function analyzer 414 may generate a diastolic function indicator using a HS metric, such as an S3 intensity or an S4 intensity. In an example, the diastolic function analyzer 414 may compute a deviation of an S3 intensity trend (or an S4 intensity trend) acquired during a detected VM session from a reference S3 template (or a reference S4 template), and the WHF detector 416 may detect an WHF event when the computed deviation satisfies a specified condition, such as exceeding a threshold. The deviation may be computed throughout the VM session, or during one or more VM phases, such as Phase II which is more closely associated with the signs of WHF in HF patients.

The diastolic function indicator may be represented by a linear or nonlinear combination of S3 and S4 metrics. In an example, the diastolic function analyzer 414 may compute a ratio of an S3 intensity to an S4 intensity (S3/S4 ratio). The S3 intensity and S4 may respectively correspond to the "E" wave and "A" wave as seen in a Doppler echocardiograph. The "E" wave and "A" wave are two peaks on the transmitral flow profile derived from the echocardiograph. The "E" wave arises due to early passive diastolic filling, which accounts for 70-75% of the ventricular filling during this phase. The "A" wave arises due to atrial contraction, forcing approximately 20-25% of stroke volume into the ventricle. A ratio of "E" wave to "A" wave (hereinafter the "E/A ratio") represents a relative velocity of blood flow during the early and late phases of diastole. In a subject with normal diastolic function, the E/A ratio is within a range of approximately between 1 and 1.5. In HF patients with impaired relaxation (a relatively mild diastolic dysfunction), the left ventricular wall can become stiff such that it impairs proper filling. The "E" wave may become reduced, representing a transmitral velocity that may be even slower than the subsequent "A" wave velocity. Correspondingly, the E/A ratio may be less than one.

The S3/S4 ratio may be indicative of or correlated to the E/A ratio. In an example, the WHF detector may compare the S3/S4 ratio obtained during the VM to a healthy value range defined by a lower threshold value and a higher threshold value. The WHF detector 416 may detect WHF when the S3/S4 satisfies a specific condition, such as exceeding a threshold value or falls within a specified value range. For example, if S3/S4 ratio falls within the healthy value range, then no substantial diastolic dysfunction is detected. If S3/S4 exceeds the upper threshold value, restrictive ventricular filling is indicated. If S3/S4 falls below the lower threshold value, impaired diastolic function is indicated.

FIG. 4B illustrates a VM-based event detector 420 configured to detect a target event of syncope using the physiologic responses to the VM. As previously discussed, majority of syncope are non-cardiac in nature, including neurally mediated syncope (or vasovagal syncope, VVS), and orthostatic syncope (or orthostatic hypotension, OH). The VVS is a disorder of the autonomic regulation of postural tone, and may be related to vasovagal, carotid sinus, or situational causes of hypotension.

The VM-based event detector 420 includes autonomic function analyzer 424, which is an embodiment of the physiologic response analyzer 224, coupled to the VM detector 222 and configured to detect a cardiovascular or autonomic function indicator during the detected VM. In one example, the cardiovascular or autonomic function indicator includes a Valsalva ratio, which generally refers to a ratio of the longest cardiac cycle (R-R interval) at Phase IV of the VM following the liberation of straining to the shortest cardiac cycle at Phase II of the VM during straining ($RR_{IV}/RR_{II}$). The Valsalva ratio reflects both parasympathetic (vagal) and sympathetic function. The normal HR response during the VM is an increase in HR (i.e., shortening of RR interval) during Phase II in response to the fall in blood pressure, and the baroreflex response to the blood pressure overshoot in Phase IV is transient bradycardia (i.e., a decrease in HR or lengthening of RR interval). In VVS patients, there can be a loss of both the blood pressure overshoot and the reflex bradycardia, thereby a lower than normal Valsalva ratio. The autonomic function analyzer 424 may compute the Valsalva ratio using heart rates (or RR intervals) measured during the detected VM session, and the syncope detector 426 may detect the VVS when the computed Valsalva ratio satisfies a specific condition, such as falling below a threshold or falls within a value range. An example of the Valsalva ratio threshold is approximately between 1.1 and 1.2.

The syncope detector 426 may also differentially diagnose orthostatic syncope (or OH), which is clinically a confounder of VVS. Compared to a healthy subject, a patient with OH may not be able to generate appropriate sympathetically mediated vasoconstriction in response to the initial hypotension at Phase I. Patients with OH also lack blood pressure recovery at the late Phase II, and the blood pressure overshoot at Phase IV. Rather, the BP slowly drifts back up to baseline after the Valsalva-induced hypotension. The autonomic function analyzer 424 may generate the cardiovascular or autonomic function indicator using a HS metric, such as S2 intensity. S2 intensity is correlated with blood pressure during the VM. The vasovagal function analyzer 424 may determine abnormality of S2 response, such as computing a deviation of a S2 intensity trend during the detected VM (or during one or more VM phases) from a reference S2 intensity template acquired from healthy population. The syncope detector 426 may detect orthostatic syncope if the deviation of S2 intensity from the template satisfies a specified condition, such as exceeding a threshold.

FIG. 4C illustrates a VM-based event detector 430 is configured to detect a constipation episode using the detected physiologic responses to VM. Constipation generally refers to difficulty or slowing of passing the stool and less frequent (e.g., three or fewer in a week) bowel movements than normal. A VM session is typically invoked during defecation. During VM, with the holding of the breath and straining, the diaphragm is forced downwards by the increased pressure inside the thoracic cavity, thereby helping evacuating wasteWhen constipation occurs, excessive straining, expressed in intensively repeated VM, is needed for emptying the bowels. The increased pressure in the thoracic cavity reduces the amount of blood flowing into the thoracic cavity, especially in the veins leading to the right atrium of the heart. Although a healthy subject may withstand the intensive and repeated straining at defecation, for a cardiac patient (e.g., HF) with compromised cardiovascular system, constipation may increase the risk of defecation syncope attack or death. The intensive and repeated VM during constipation may also cause blood clots to detach, bleeding, irregular heart rhythms and cardiac arrest.

The VM-based event detector 430 may be used to monitor bowel movement regularity and assess severity of constipation. The VM-based event detector 430 includes the physiologic response analyzer 224 couple to the VM detector 222, and a constipation detector 436 configured to constipation. In an example, the VM detector 222 may detect onset of a VM session, such as by using HS metrics. The physiologic response analyzer 224 may determine duration of a VM session, or frequency of VM sessions such as by counting the VM sessions as detected by the VM detector 222 during a specified time period. The constipation detector 436 may detect a constipation episode, or to generate a constipation severity indicator, using the frequency of VM and duration of each VM session. For example, frequent VM sessions that sustained for an extended period of time, with each VM having a short duration, may be indicative of an incidence of constipation.

The physiologic response analyzer 224 may additionally or alternatively determine, using HS metrics or other physiologic signals (e.g., heart rate or blood pressure signal), the hemodynamic responses during the straining (e.g., Phases I-II) and relaxation (e.g., Phases III-IV) of each detected VM session. In an example, the physiologic response analyzer 224 may determine changes in heart rate (FIR) or changes in HS metrics (e.g., S1 or S2 intensity) at one or more VM phases, or duration of one or more VM phases, such as the straining period (e.g., Phases I and II) of the VM. A more severe constipation may be accompanied by more significant hemodynamic change from a reference baseline, or a substantially longer straining period of a VM. The constipation detector 436 may determine the constipation severity indicator using a comparison of the determined changes in HR or the change in HS metrics to respective thresholds, or a comparison of straining period (e.g., duration of Phases I and II) of a VM session to a threshold.

Figure 5:
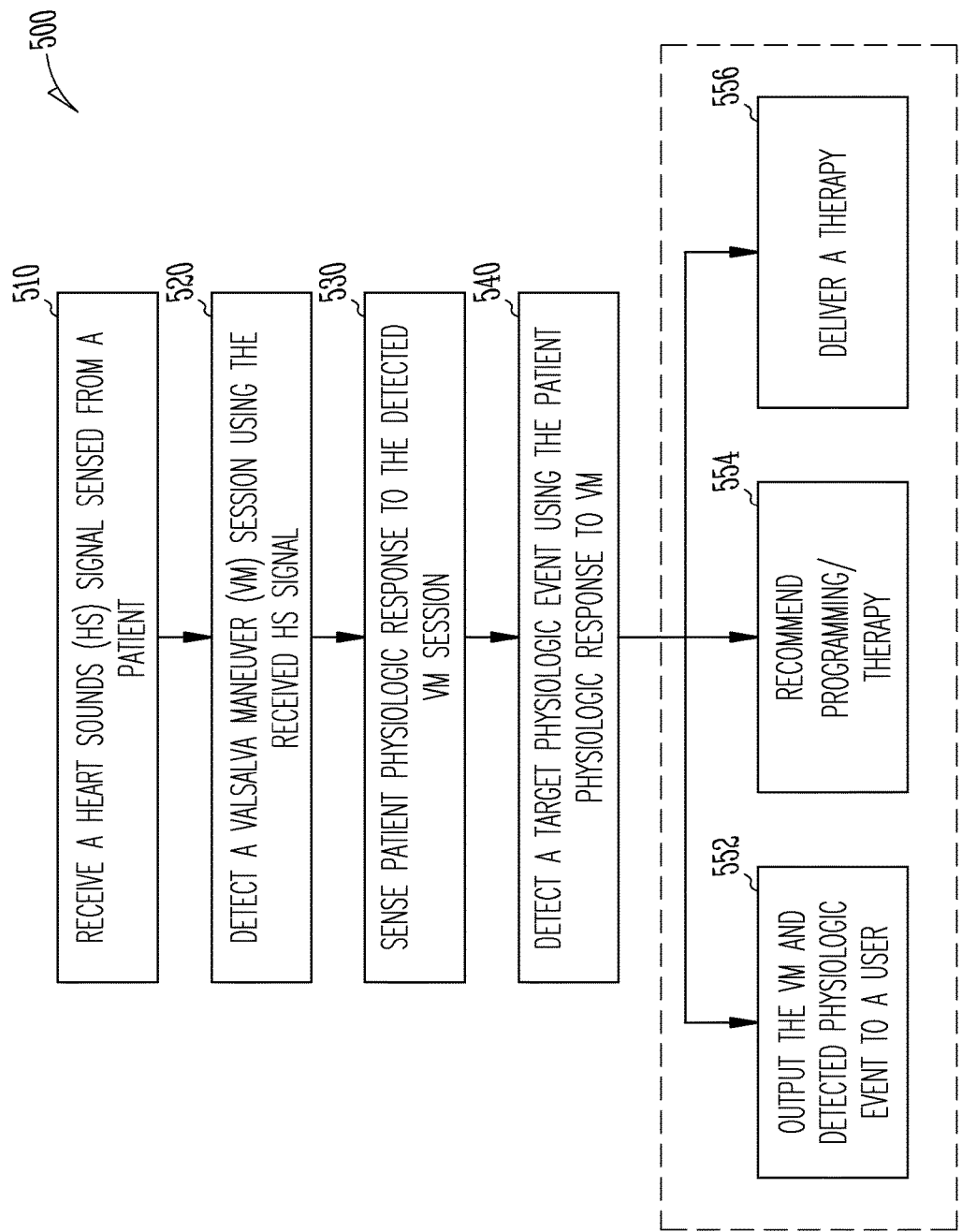
FIG. 5 illustrates generally an example of a method for monitoring a physiologic response to VM in a patient.

FIG. 5 illustrates generally an example of a method 500 for monitoring a physiologic response to VM in a patient. In an example, the method 500 may be implemented in and executed by the cardiac arrhythmia detection circuit 160 in the AMD 110, the external system 130, or the VM detector and analyzer system 200.

The method 500 commences at step 510, where one or more physiologic signals including a heart sounds (HS) signal may be received. The HS signal may be sensed using a HS sensor, such as an accelerometer, an acoustic sensor, a microphone, a piezo-based sensor, or other vibrational or acoustic sensors that are included in the AMD 110, or disposed on a lead such as a part of the lead system 108. In an example, the accelerometer may sense an epicardial or endocardial acceleration (EA) signal from a portion of a heart, such as on an endocardial or epicardial surface of one of a left ventricle, a right ventricle, a left atrium, or a right atrium. Other physiologic signal may also be received, which may include surface ECG, subcutaneous ECG, intracardiac EGM, heart rate signal, physical activity signal, or posture signal, a thoracic or cardiac impedance signal, blood pressure signal, blood oxygen saturation signal, physiologic response to activity, apnea hypopnea index, one or more respiration signals such as a respiration rate signal or a tidal volume signal, brain natriuretic peptide (BNP), blood chemical levels, etc.

At 520, a VM session may be detected using at least the received HS signal, such as by using the VM detector 222. The VM session may occur naturally in an ambulatory setting. One or more HS components may be detected from the HS signal, including a first (S1) heart sound, a second (S2) heart sound, a third (S3) heart sound, or a fourth (S4) heart sound using respective time windows. One or more HS metrics may be generated using the detected HS components, which may include, by way of example and not limitation, an intensity (e.g., amplitude or signal energy under the curve) of a HS component, one or more HS-based cardiac timing intervals such as PEP, STI, LVET, DTI, as discussed above with reference to FIG. 2, or composite HS metrics.

Various HS metrics may be indicative of or correlated with the hemodynamic profiles at various VM phases, including one or more of Phases I-IV. In an example, Phase I of VM may be recognized using an increase in S1 intensity accompanied by a decrease in S2 intensity. Additionally or alternatively, an increase in S3 intensity or an increase in S4 intensity, which correspond to immediate accumulation of blood in the left atrium of the heart and thus a rise in LAP, may also be used to detect VM Phase I. In an example, Phase II of the VM may be recognized using a decrease in S1 intensity and an increase in S2 intensity. The decrease in S1 intensity corresponds to reduced stroke volume and cardiac output, which leads to reduced cardiac contraction. The increase in S2 intensity at Phase II corresponds to the rise in blood pressure due to vasoconstriction to compensate for the drop in cardiac output. Phase III of VM is characterized by thoracic pressure release, and widening of intrathoracic arteries and aorta. In an example, Phase III of VM may be recognized using a decrease in S3 intensity or a decrease in S4 intensity. which reduces LAP and end-diastolic left ventricular pressure. S3 and S4 intensity may each indicate diastolic function of a heart, and is correlated to left-ventricular filling pressure or the left atrial pressure (LAP) at the end of diastole. In another example, Phase IV of the VM may be recognized using an increase in S1 intensity accompanied by an increase in S2 intensity. This corresponds to the recovery of cardiac output and blood pressure at the closing phase of VM.

Additional physiologic information may be used to improve the HS-based VM session. For example, physical activity, posture, or respiration rate or pattern, as discussed above with reference to FIG. 3, may be used to confirm a VM session, or to improve quality of the HS data acquired during the VM session. In an example, detection of VM or one or more VM phases based on HS may be initiated when a low activity level, an upright posture, or a forced breathing have been detected. Using the information of physical activity, posture, or respiration may help reduce false positive detections of VM sessions At 530, physiologic response to the VM session may be sensed, such as by using the physiologic response analyzer 224. Heart sounds, either the same signals used for detecting the VM session, or different HS signals acquired by the same HS sensors that provide the HS signal for detecting the VM session, may be used to characterize the physiologic response to the detected VM. In an example, a cardiovascular or autonomic function indicator may be generated based on a comparison of the sensed physiologic signal to a reference VM response, also referred to as a VM response template. The VM response template may be generated using physiologic data (e.g., HS data) acquired from the patient during historical VM sessions, thus representing the patient's baseline VM response. Alternatively, the VM response template may be generated using data from population during the VM sessions, thus presenting a "normal" VM response. The cardiovascular or autonomic function indicator may be represented by a degree of deviation (e.g., accumulated difference over time) of the patient physiologic data trend (e.g., a S1 intensity trend or a S2 intensity trend) from the VM response template.

At 540, a target physiologic event may be detected using the patient physiologic response to VM (e.g., the cardiovascular or autonomic function indicator as discussed above), such as by using the target event detector 226. In an example, S3 and S4 heart sound components may be detected from a HS signal sensed during the detected VM session. A diastolic dysfunction indictor may be generated using a ratio of the S3 intensity to the S4 intensity. The S3/S4 ratio may be indicative of or correlated to the E/A ratio, a metric in Doppler echocardiograph that represents a relative velocity of blood flow during the early and late phases of diastole. A WHF event may be detected using the generated diastolic dysfunction indictor.

The cardiovascular or autonomic function indicator generated at 530 may be used to detect a syncope or pre-syncope event. An example of the cardiovascular or autonomic function indicator includes a Valsalva ratio, that is, a ratio of the longest cardiac cycle (R-R interval) at Phase IV of the VM following the liberation of straining to the shortest cardiac cycle at Phase II of the VM during straining ($RR_{IV}/RR_{II}$). A vasovagal syncope (VVS) may be detected when the computed Valsalva ratio satisfies a specific condition, such as falling below a threshold or falling below a threshold or falls within a value range. In another example, the cardiovascular or autonomic function indicator includes S2 intensity, which is correlated with blood pressure during the VM. An orthostatic syncope (or orthostatic hypotension, OH) may be detected if the deviation of S2 intensity from the VM response template satisfies a specified condition, such as exceeding a threshold.

Additionally or alternatively, a constipation episode may be detected using the detected physiologic responses to VM at 540. When constipation occurs, excessive straining, expressed in intensively repeated VM, is needed for emptying the bowels. The increased pressure in the thoracic cavity reduces the amount of blood flowing into the thoracic cavity, especially in the veins leading to the right atrium of the heart, and increase the risk of defecation syncope attack or death for patients with compromised cardiovascular system. Onset, duration, and frequency of repeated VM sessions may be detected such as using the HS metrics as discussed above. Constipation severity may be quantified using, for example, frequency of VM and duration of each VM session. For example, more frequent VM sessions that sustained for an extended period of time, with each VM having a short duration, may be indicative more severe constipation condition.

The detected VM session, the physiologic response to VM, and the detected target physiologic event, may be provided to one or more of the processes 552, 554, or 556. At 552, the detected VM and the detected physiologic event, among other information, may be output to a user, such as displayed on a display unit of the user interface 230. In some examples, a hard copy of the detection information may be generated. In various examples, alerts, alarms, emergency calls, or other forms of warnings to signal may be generated to warn the system user about the detected target event. At 554, a recommendation may be generated and provided to a user. The recommendation may include one or more of further diagnostic tests to be performed, initiating a therapy to treat the detected event, changing parameters in the therapy provided by an implanted device, the prescription to get a device implanted, the initiation or change in a drug therapy, or other treatment options of a patient. At 556, a therapy may be delivered to the patient in response to the detected physiologic event, or when the detected cardiovascular or autonomic function indicator satisfies a specific condition (e.g., indicating a blunted vasovagal response or autonomic function), such as via the optional therapy circuit 240 as illustrated in FIG. 2. Examples of the therapy may include electrostimulation therapy delivered to the heart, a nerve tissue, other target tissues, a cardioversion therapy, a defibrillation therapy, or drug therapy including delivering drug to the patient. In some examples, the therapy circuit 240 may modify an existing therapy, such as adjust a stimulation parameter or drug dosage.

Figure 6:
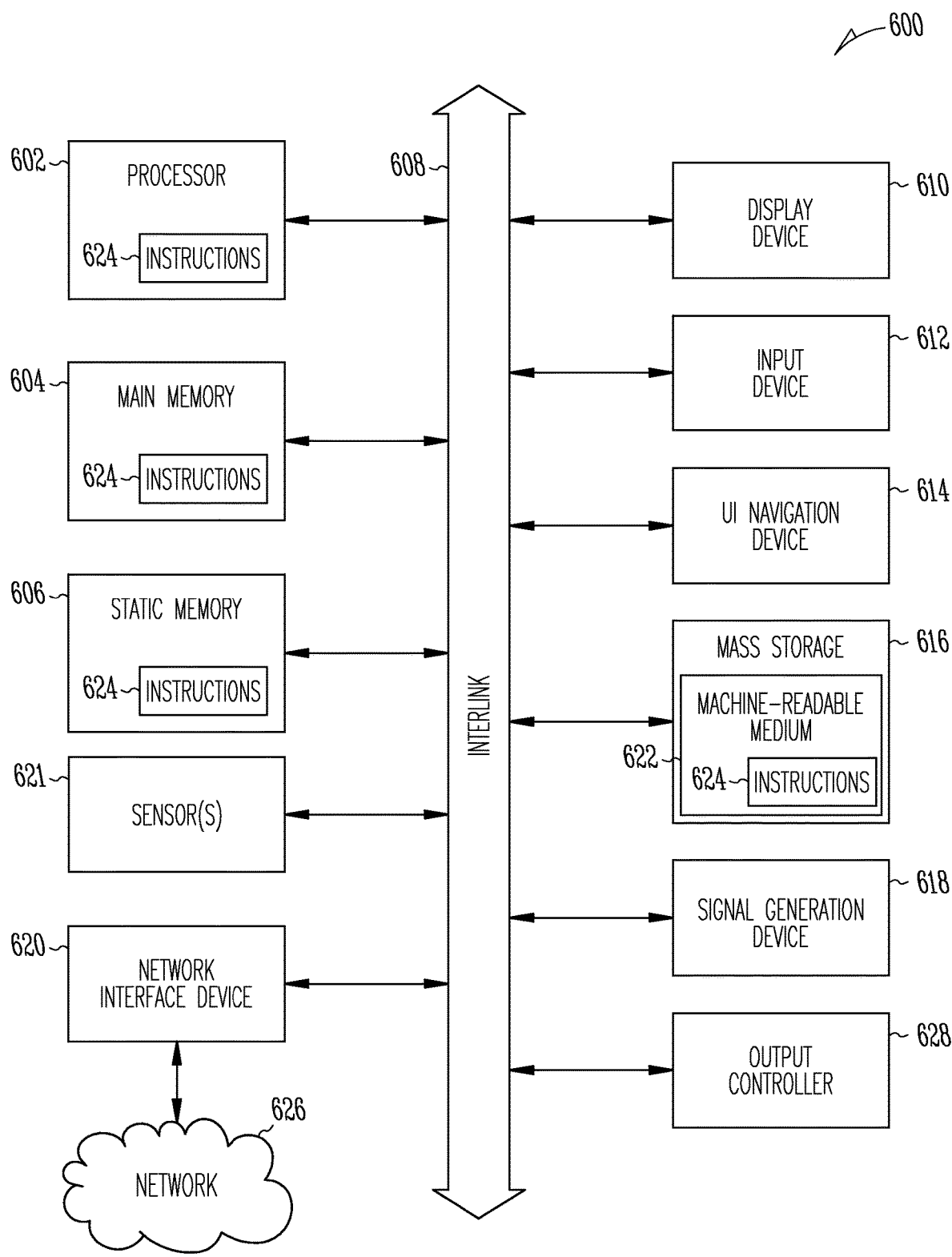
FIG. 6 illustrates generally a block diagram of an example machine upon which any one or more of the techniques (e.g., methodologies) discussed herein may perform.

FIG. 6 illustrates generally a block diagram of an example machine 600 upon which any one or more of the techniques (e.g., methodologies) discussed herein may perform. Portions of this description may apply to the computing framework of various portions of the LCP device, the AMD, or the external programmer.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for monitoring a physiologic response to a Valsalva maneuver (VM) in a patient, the system comprising:
   a VM detector circuit configured to detect a VM session using a heart sound (HS) signal sensed from the patient;
   a physiologic response analyzer circuit configured to sense a physiologic signal during the detected VM session; and
   a physiologic event detector configured to detect a target physiologic event using the sensed physiologic signal during the detected VM session.

2. The system of claim 1, wherein the VM detector circuit is configured to recognize one or more VM phases using a HS metric based on one or more of first (S1), second (S2), third (S3), or fourth (S4) heard sound component from the sensed HS signal, the VM phase including sequentially arranged first, second, third, or fourth VM phases.

3. The system of claim 2, wherein the VM detector circuit is configured to detect one or more of:
   the first VM phase using an increase in S1 intensity and a decrease in S2 intensity, or an increase in S3 intensity or an increase in S4 intensity;
   the second VM phase using a decrease in S1 intensity and an increase in S2 intensity;
   the third VM phase using a decrease in S3 intensity or a decrease in S4 intensity; or
   the fourth VM phase using an increase in S1 intensity and an increase in S2 intensity.

4. The system of claim 2, wherein the VM detector circuit is configured to detect the VM session further using one or more of:
   a physical activity level below a specific threshold;
   an upright posture; or
   a respiratory pause.

5. The system of claim 2, wherein the physiologic event detector is configured to detect the target physiologic event including a constipation episode.

6. The system of claim 1, wherein the physiologic response analyzer circuit is configured to generate a cardiovascular or autonomic function indicator using the sensed physiologic signal during the detected VM session, the sensed physiologic signal includes one or more of a HS signal and a heart rate signal.

7. The system of claim 6, wherein the physiologic response analyzer circuit is configured to generate the cardiovascular or autonomic function indicator using a comparison of the sensed physiologic signal during the detected VM session to a Valsalva response template.

8. The system of claim 6, wherein the physiologic event detector is configured to detect a syncope using the generated cardiovascular or autonomic function indicator.

9. The system of claim 8, wherein the physiologic event detector is configured to detect: a vasovagal syncope using a Valsalva ratio between heart rates at different VM phases during the detected VM session, or an orthostatic syncope using a S2 intensity trend during the detected VM session.

10. The system of claim 1, wherein:
    the physiologic response analyzer circuit is configured to detect S3 intensity and S4 intensity from a HS signal sensed during the detected VM session, and to generate a diastolic dysfunction indictor using a ratio of the S3 intensity to the S4 intensity; and
    the physiologic event detector is configured to detect a worsening heart failure (WHF) event using the generated diastolic dysfunction indictor.

11. The system of claim 1, further comprising a therapy circuit configured to initiate or adjust a therapy to the patient in response to the detected target physiologic event.

12. The system of claim 1, further comprising an ambulatory medical device (AMD) including the VM detector circuit and the physiologic response analyzer circuit, the AMD configured to monitor a patient physiologic response to the detected VM session.

13. A method for monitoring a physiologic response to a Valsalva maneuver (VM) in a patient, the method comprising:
    detecting, via a VM detector circuit, a VM session using a heart sound (HS) signal sensed from the patient;
    sensing, via a physiologic response analyzer circuit, a physiologic signal during the detected VM session; and
    detecting, via a physiologic event detector, a target physiologic event using the sensed physiologic signal during the detected VM session.

14. The method of claim 13, wherein detecting the VM session includes recognizing one or more VM phases using a HS metric based on one or more of first (S1), second (S2), third (S3), or fourth (S4) heard sound component from the sensed HS signal, the VM phase including sequentially arranged first, second, third, or fourth phases.

15. The method of claim 14, wherein recognizing the one or more VM phases includes detecting one or more of:
    the first VM phase using an increase in S1 intensity and a decrease in S2 intensity, or an increase in S3 intensity or an increase in S4 intensity;
    the second VM phase using a decrease in S1 intensity and an increase in S2 intensity;
    the third VM phase using a decrease in S3 intensity or a decrease in S4 intensity; or
    the fourth VM phase using an increase in S1 intensity and an increase in S2 intensity.

16. The method of claim 13, wherein detecting a VM session further includes detecting one or more of:
    a physical activity level below a specific threshold;
    an upright posture; or
    a respiratory pause.

17. The method of claim 13, comprising generating a cardiovascular or autonomic function indicator using a comparison of the sensed physiologic signal during the detected VM session to a Valsalva response template, the sensed physiologic signal includes one or more of a HS signal and a heart rate signal.

18. The method of claim 17, wherein detecting the target physiologic event includes detecting a syncope using the generated cardiovascular or autonomic function indicator.

19. The method of claim 13, wherein detecting the target physiologic event includes:
    detecting S3 intensity and S4 intensity from a HS signal sensed during the detected VM session;
    generating a diastolic dysfunction indictor using a ratio of the S3 intensity to the S4 intensity; and
    detecting a worsening heart failure (WHF) event using the generated diastolic dysfunction indictor.

20. The method of claim 13, comprising initiating or adjusting a therapy to the patient in response to the detected target physiologic event.

* * * * *